United States Patent [19]

Cleland, Sr., deceased et al.

[11] Patent Number: 6,135,153
[45] Date of Patent: Oct. 24, 2000

[54] ANESTHESIA DELIVERY SYSTEMS AND METHODS

[76] Inventors: John Cleland, Sr., deceased, late of Oregon City, Oreg.; by John Cleland, Jr., legal representative, 605 High St., Oregon City, Oreg. 97045; Orville Brack, deceased, late of Lake Oswego, Oreg.; by Glenn Brack, legal representative, 754 Oak Meadows Ct., Lake Oswego, Oreg. 97034

[21] Appl. No.: 09/178,204

[22] Filed: Oct. 23, 1998

Related U.S. Application Data

[60] Provisional application No. 60/070,372, Jan. 2, 1998.
[51] Int. Cl.$^7$ ..................................................... F16K 11/08
[52] U.S. Cl. ................................ 137/625.46; 137/625.47
[58] Field of Search .......................... 137/625.46, 625.47

[56] References Cited

U.S. PATENT DOCUMENTS

| | | |
|---|---|---|
| 743,714 | 11/1903 | Guese ................................. 137/625.47 |
| 4,604,093 | 8/1986 | Brown et al. . |
| 4,822,344 | 4/1989 | O'Boyle . |
| 4,874,386 | 10/1989 | O'Boyle . |
| 4,898,669 | 2/1990 | Tesio . |
| 4,901,763 | 2/1990 | Scott ................................... 137/625.47 |
| 4,917,687 | 4/1990 | O'Boyle . |
| 5,014,750 | 5/1991 | Winchell et al. . |
| 5,105,851 | 4/1992 | Fogelman ........................... 137/625.11 |
| 5,816,290 | 10/1998 | Altshuler ............................ 137/625.47 |

*Primary Examiner*—John Fox
*Attorney, Agent, or Firm*—Kolisch, Hartwell, Dickinson, McCormack & Heuser

[57] ABSTRACT

Improvements relating to devices and methods for carrying out a double-catheter epidural procedure are provided. An integrated valve assembly employs a manipulable dial for selectively connecting an anesthesia input port to one of plural output ports to thereby provide anesthesia delivery access through a catheter to a targeted location in a patient's epidural space.

6 Claims, 4 Drawing Sheets

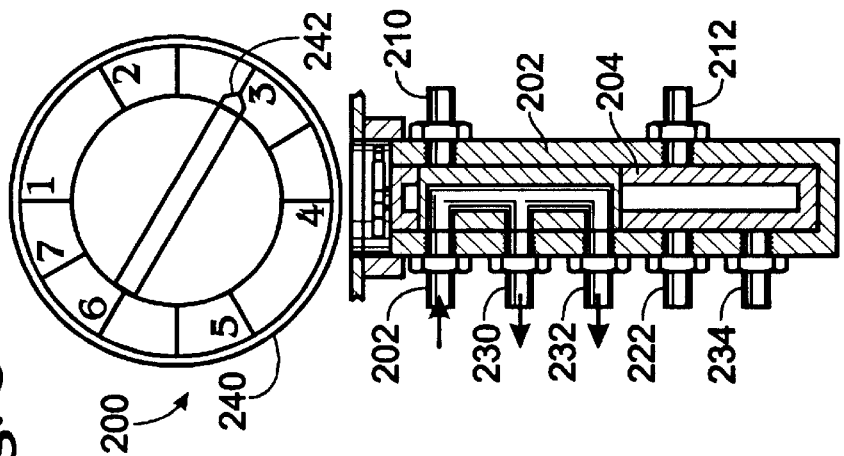
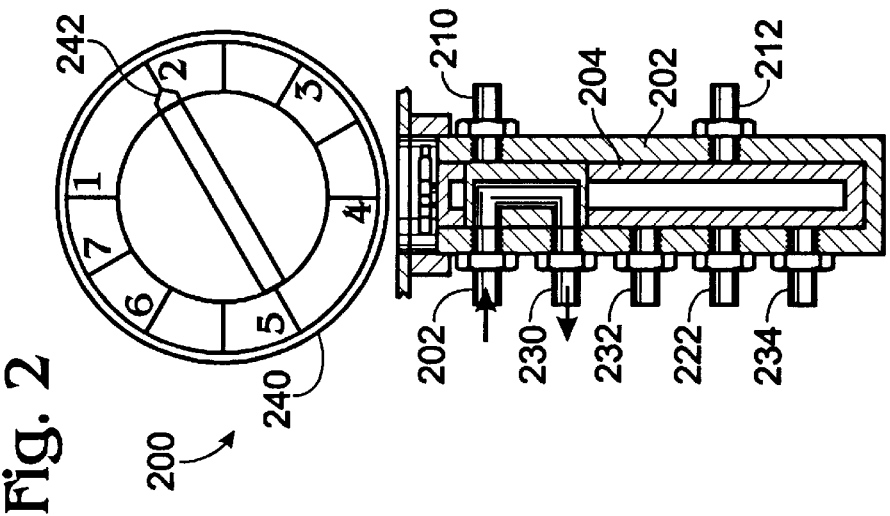
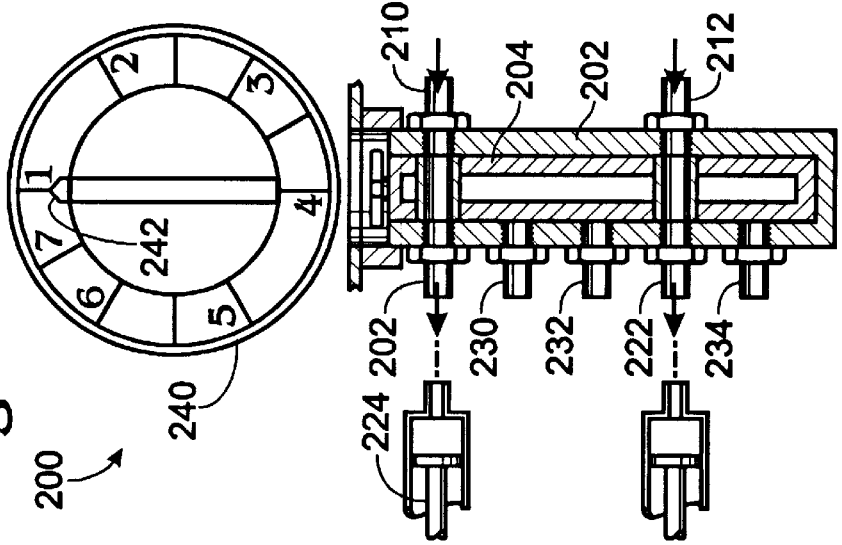

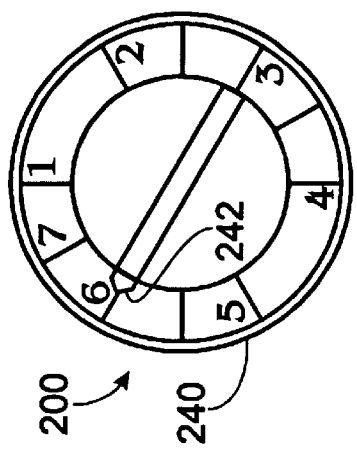
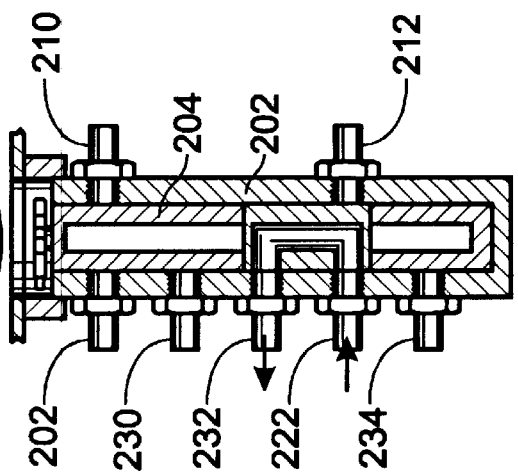
Fig. 4
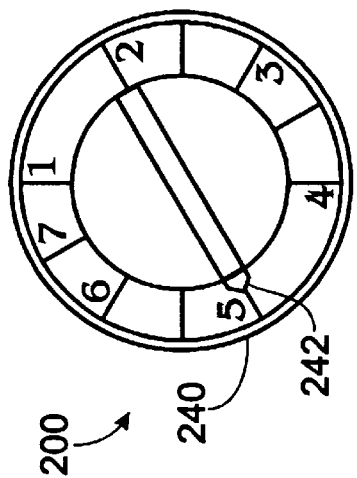
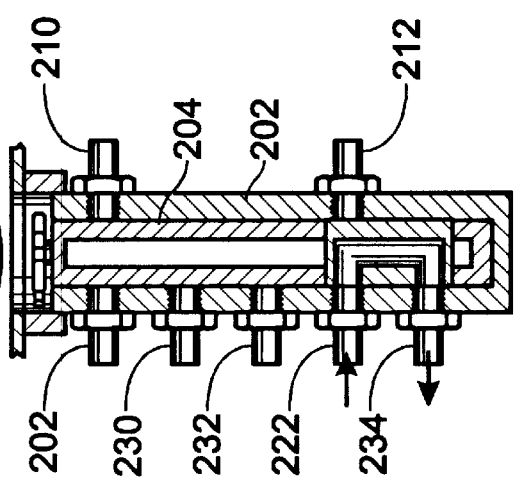
Fig. 5
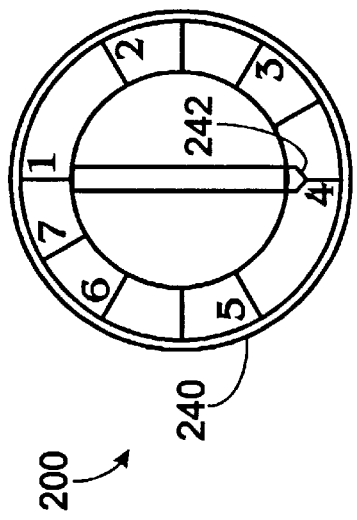
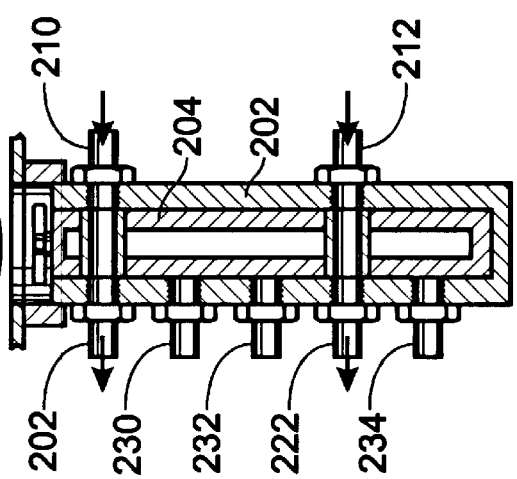
Fig. 6

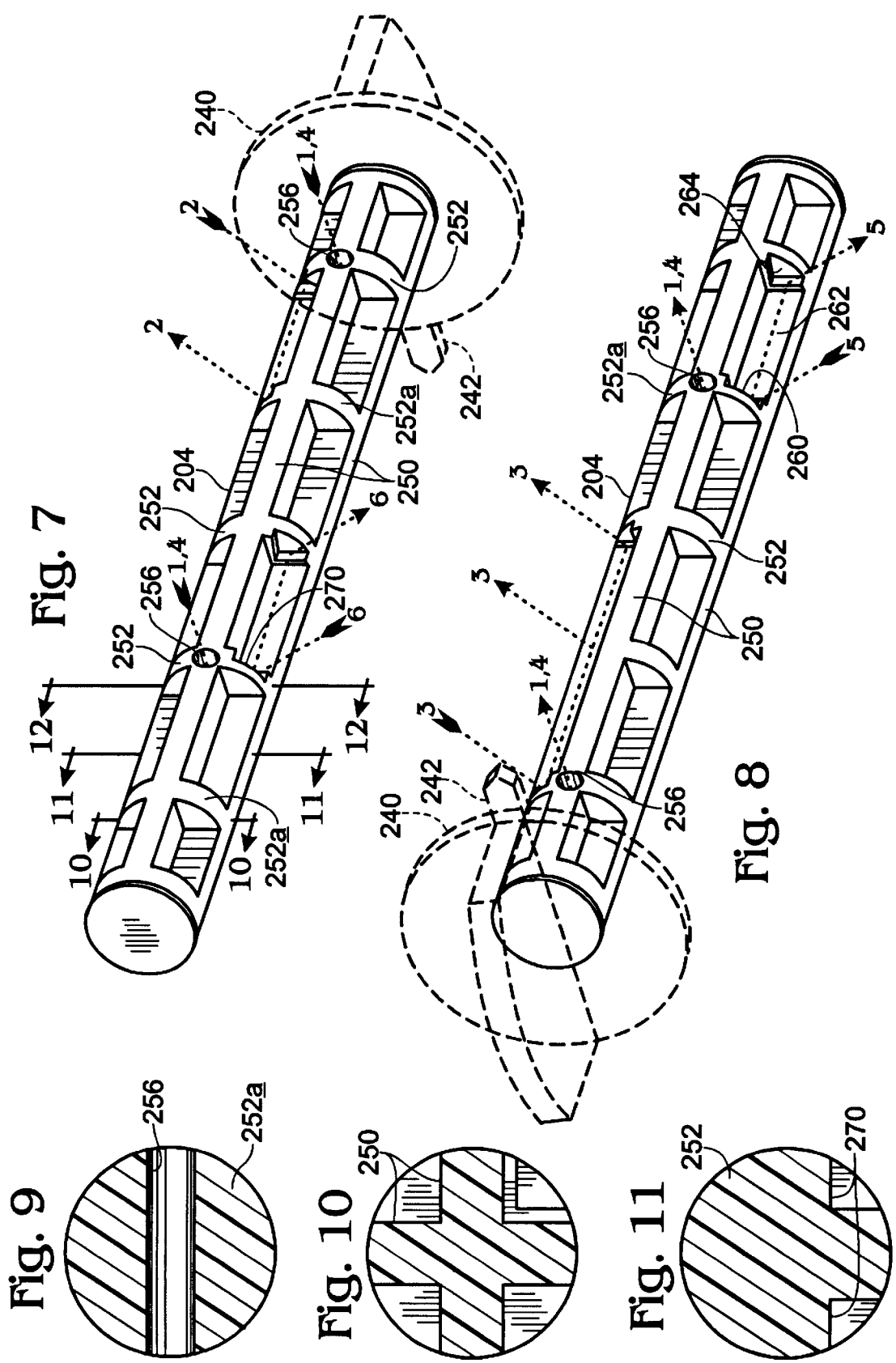

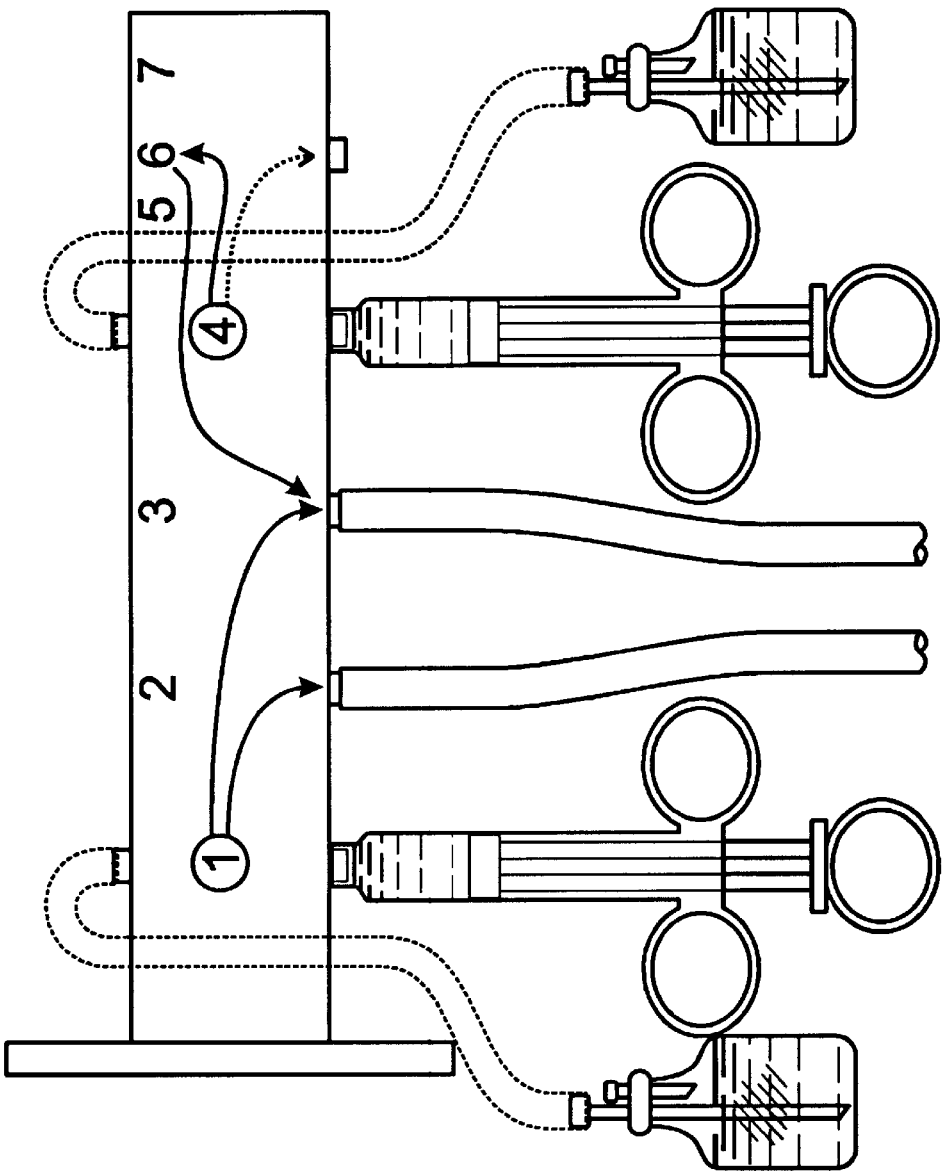
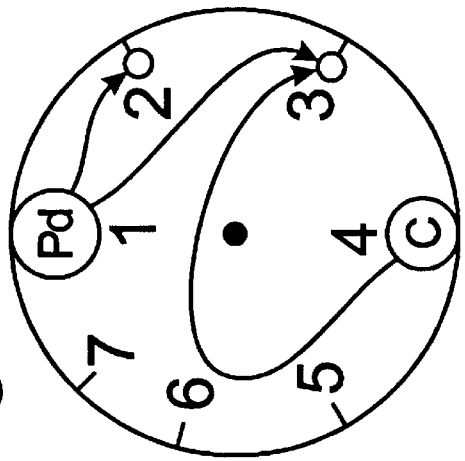
Fig. 12
Fig. 13

ANESTHESIA DELIVERY SYSTEMS AND METHODS

CROSS-REFERENCE TO RELATED APPLICATION

This application claims priority from U.S. Provisional Application Ser. No. 60/070,372, filed Jan. 2, 1998.

FIELD OF THE INVENTION

The invention relates to a system and method of delivering anesthesia. Most specifically, it involves devices and techniques for administering anesthesia segmentally and selectively through more than one catheter to control the pain of labor and delivery, which progresses from one group to involve a second group of spinal nerve segments. It has also demonstrated value for cesarean section and postpartum tubal ligation, and during and after many gynecological and general surgical procedures. In a broader sense, it offers a practical means: (a) for controlling pain taking origin from areas of the body from nipple-line down with minimization of involvement of other functions, and (b) for treating other maladies that can be helped by application of local anesthetics or other medication to specific spinal nerve roots. A valve device of the invention also has potential value in applications outside of the medical field.

BACKGROUND AND SUMMARY OF THE INVENTION

For seventy years, epidural procedures, first by single injection, then with needles and catheters, have been used to block labor pain. By placing an anesthetic solution not in the fluid-filled spinal canal, but in the epidural space outside it, sufficient localization can be achieved, when helped by characteristics of the anesthetic and features of the anatomy, to block spinal nerve trunks carrying pain from involved structures to the spinal cord without interfering with nerve functions which should remain intact to mediate labor or other processes. While epidural anesthesia is the commonest method of controlling childbirth today in most developed countries, it can disappoint the patient and physician alike by being variable in its effectiveness from one patient to another, or by interrupting to a degree the important labor functions: (1) increasing the need for cesarean section or instrumental delivery with vacuum extractor or forceps,—with their potential of increasing morbidity, or (2) creating an additional risk when depression of labor mechanisms are superimposed on a medical or obstetric difficulty accompanying, or arising in, labor.

SUMMARY OF THE INVENTION

The present invention provides anesthesia delivery through a single catheter controlled by a single integrated valve unit which basically includes an outer housing having a first input port, a first output port, and a first fluid-measuring device port. A fluid-holding and measuring device, such as a syringe or Harvard pump, is connected to the first fluid-measuring device port A cylindrical fluid-channeling member is located substantially within the outer housing. The channeling member can be rotated to first, second and third positions, so that the first fluid-measuring device port communicates with the first fluid input port when the channeling member is in the first position. The first fluid-measuring device port communicates with the first output port when the channeling member is at the second position. The first fluid-measuring device port communicates with no port when the channeling member is at the third position.

When the fluid delivery device is being used with a single solution in a double-catheter epidural procedure, the outer housing has at least one additional output port, i.e., a second output port. The channeling member is rotatable to a fourth position, and has a conduit structure allowing communication between the first fluid-measuring device and the second output port when the channeling member is at the fourth position. Thus, rotation of the channeling member effectively allows the user to deliver fluid from the input port to the fluid-measuring device, and then direct a measured quantity of fluid into either the first or second output port,—to one of the two catheters.

As a developed embodiment of the fluid-delivery device where more than one solution is used, when the device is being used to deliver more than one solution, the housing has a second input port, a third output port, and a second fluid-measuring device port. The channeling member is rotatable to a fifth, sixth, and seventh position relative to the housing. The conduit structure of the channeling member allows communication between the second input port and the second fluid-measuring device port when the channeling member is in the fourth position. When the channeling member is in the fifth position, the conduit structure allows communication between the second fluid-measuring device port and the third output port. When the channeling member is in the sixth position, the conduit structure allows communication between the second fluid-measuring device port and the second output port. This design allows flexibility for rapid and aseptic delivery of different fluids through either of the two catheters. Rotation of the channeling member relative to the housing is accomplished by a manipulable dial.

Sharply-localized blocks are achieved with the double-catheter method for obstetrics (as aforementioned) by administering a mixed solution with unusual characteristics of penetrance and localization that facilitated (a) the accurate mapping of dermatomes, (b) definition of the nerve roots involved in labor, and (c) optimal restriction of block to desired nerve roots. It consisted of procaine 4%, mepivacaine 0.6%, epinephrine 5 micrograms per cc, and norepinephrine 2 micrograms per cc. While no complications were ever encountered with this solution, it continues to be unavailable as a marketed item. Closest to it in qualities of localization and penetrance would likely be the widely-marketed and readily-available anesthetic drug bupivacaine [marcaine®], which produced satisfactory results in the Clelands' experience, and has been used successfully in a series by Drs. Bonica and McDonald. Modifications to be observed in its use would include slightly larger anesthetic doses and inclusion of T10 in the epidural block. Variations from our evolved method will be described.

For surgery and postoperative analgesia applications, the system uses the same equipment and method as for obstetrics, but with different solutions and injection schedules. Our surgical solutions localize sufficiently well to show an advantage in blood pressure maintenance. The postoperative solution would permit pain-free breathing and ambulation of gynecological surgery patients. Solutions of this degree of localization are not yet commercially available, but advantage is seen for when they are. At this time, the repeated injections may be given using available but less-well-localizing solutions though one or two catheters.

FIGS. 1–6 are sectional schematic views of the valve device-part of the present invention for controlling delivery of anesthetic in a double-catheter procedure.

FIGS. 7 and 8 are perspective views of the internal channeling member employed in the anesthesia delivery device illustrated in FIGS. 1–6.

FIGS. 9–11 are cross-sectional views taken at the designated locations along the length of the channeling member illustrated in FIGS. 7 and 8.

FIG. 12 shows the valve apparatus for epidural and caudal block using the Cleland localizing solution. Bupivacaine 0.25 percent and 0.125 percent, respectively, (or other), may be substituted. This is an aseptic semi-closed system [the bottles have airways with micropore filters] and there are, basically, two syringes and two solutions.

FIG. 13 is a front view of the dial on the valve apparatus of FIG. 12.

DESCRIPTION OF TECHNIQUE FOR USE OF THE INVENTION

The present invention provides a rapid fluid delivery system and method which is potentially useful in not only obstetrical, but a variety of surgical, diagnostic, and medical therapeutic uses,—as well as other potential applications. Details and use of the invention to be described in the next passage, however, relate specifically to the carrying-out of a double-catheter epidural procedure to control the pain of childbirth.

Operation of the Multi-Port Measured Fluid Distribution Valve

We will first discuss the mechanism of operation of the valve in general terms—then in specific terms for its use for labor and delivery and other tested applications. As indicated above, the catheters are connected to tubings from the output ports of an integrated fluid delivery device,—the valve assembly. The valve assembly is made preferably of an injection molded polymer resin. FIGS. 1–6 show schematically an integrated valve assembly which facilitates fluid delivery through both the aforementioned catheters. Valve assembly 200 includes an outer cylindrical housing 202. The latter contains an inner cylindrical channeling member 204 which is rotatable within and relative to housing 202. Valve assembly 200 has two input ports, 210 and 212, each of which can be connected to different anesthetic (or other) liquid supplies or sources. As shown in FIGS. 1–6, the left side of housing 202 is provided with two fluid-measuring device ports, 220 and 222, directly across from input ports 210 and 212, respectively. FIG. 1 shows fluid delivery devices 224 and 226, such as syringes, which are connectable to fluid delivery device ports 220 and 222, respectively. Provided on the left side of housing 202 are three fluid output ports, 230, 232 and 234. Dial 240 is connected to the inner channeling member 204 so that a person can manipulate dial 240 and thereby cause channeling member 204 to rotate relative to housing 202.

Seven positions are shown on dial 240. As a pointer 242 is dialed to different positions, channeling member 204 forms different conduit communication routes between different input and output ports in the valve assembly 200. As shown in FIG. 1, when pointer 242 on dial 240 is in the first position, the conduit structure of channeling member 204 connects input port 210 to fluid-measuring device port 220, and fluid input port 212 to fluid-measuring device port 222. As shown in FIG. 2, when indicator 242 of dial 240 is in the second position, the conduit structure of channeling member 204 connects fluid-measuring device port 220 to a first fluid output port 230. As shown in FIG. 3, when indicator 242 of dial 240 is in the third position, the conduit structure of channeling member 204 connects fluid-measuring device port 220 to the second fluid output port 232. As shown in FIG. 4, when indicator 4 of dial 240 is in the fourth position, the conduit structure of channeling member 204 connects fluid input ports 210 and 212 to fluid-measuring device ports 220 and 222, respectively. Thus, the conduit structure and orientation at position 4 is functionally the same as the conduit structure and orientation in position 1. As shown in FIG. 5, when indicator 242 of dial 240 is in the fifth position, conduit structure of channeling member 204 connects fluid-measuring device port 222 to third fluid output port 234. As shown in FIG. 6, when indicator 242 of dial 240 is in the sixth position, conduit structure of channeling member 204 connects fluid-measuring device port 222 to second fluid output port 232. Finally, when indicator 242 of dial 240 is in the seventh position, all ports are closed.

FIGS. 7 and 8 show perspective views of channeling member 204. The conduit structure of channeling member 204 is set up principally through and between a set of longitudinal ribs 250 and lateral circular width-wise ribs 252. When channeling member 204 is properly inserted inside housing 202, ribs 252 line up with the various ports described above and shown in FIGS. 1–11. Lateral ribs 252 are oriented perpendicularly to longitudinal ribs 250. Lateral ribs 252a, at their point of intersection with two of the longitudinal ribs, have openings or holes 256 which allow fluid to pass from one side of the channeling member to the opposite side. Holes 256 facilitate the fluid delivery configurations shown in FIGS. 1 and 4, i.e., positions 1 and 4.

Mechanisms for delivering fluid between ports on the same side of housing 202,—i.e., between ports on the left side of housing 202, can be seen in FIGS. 7, 8 and 11. In general, notches are defined in lateral ribs 252 so that, when the dial is positioned appropriately, fluid can pass through a trough intervening two notched ribs. For example, in the lower right-hand corner of FIG. 8, arrow 5 shows the direction of fluid delivery when indicator 242 of dial 240 is in the fifth position. Fluid is permitted to flow from fluid-measuring device port 222 through notch 260 of rib 252a into trough 262, through notch 264, and finally out of output port 234 in housing 202.

For the purpose of illustrating different conduit paths, numbered arrows in FIGS. 4 and 5 show the fluid flow path through conduit structure and channeling member 204 corresponding to the various dial positions shown in FIGS. 1–11. For example, arrows 1 and 4 indicate that fluid can pass through holes 256 when indicator 242 on dial 240 is in the first and fourth positions.

FIG. 9 is a cross-section through channeling member 204 shown in FIG. 7. It shows hole 256 in lateral rib 252a.

FIG. 10 is also a cross-section through channeling member 204 showing the perpendicular orientation of longitudinal ribs 250 and lateral ribs 252.

FIG. 11 is a cross-section through channeling member 204 showing notches on opposing sides of lateral rib 252.

A. Use of Valve Apparatus for Labor and Delivery:

The double-catheter method developed into a 2-solution technique with definitive localizing solutions. (1) Preliminary steps:

Discussion of procedure with patient: analgesia is discussed in general, and the double-catheter procedure in particular. Any questions are answered. If patient wishes the procedure, we go on to the next step.

Assembly of valve components: while patient is on her left side awaiting scrub and drape, the two syringes and anesthetic bottles, and peridural and caudal tubings are assembled to the valve, which is (preferably) mounted on the head of the bed, or wrapped in two sterile towels.

Back prep and test doses: the back is sterilely prepped and draped, and catheters are placed, with patient curled up on her left side as previously described, and 2 ml peridural and caudal test doses given.

Filling of catheter tubings: using the syringe of station 1, stations 2 and 3 tubings are filled with peridural solution, with 4 ml left in the syringe. Peridural and caudal tubings are now connected to the appropriate catheters using Luer-lok connectors over the catheter ends. The caudal tubing has a fluid capacity of 2½ ml.

(1) Peridural main dose: After patient has been on her back for 10 minutes after the test dose, and dermatomes carefully checked, the main peridural dose of 4 ml is given from station 1 syringe into station 2. Three ml more peridural solution is now drawn up into the station 1 syringe.

(2) Follow up peridural doses: 3 ml solution is injected from station 1 syringe into station 2, then replacing the 3 ml in the syringe. This is repeated at 40–90 minute intervals (prn or ad lib) through labor.

(3) Transition and caudal doses: 3 options and technique now come into play,—as follows:

I. Segmental Sequential Technique (most cases)

Peridural-in-caudal tubing (transition) dose: With onset of pelvic pain prior to full cervical dilation despite regular peridural doses, or, prophylactically, 2–3 ml peridural solution is now injected from station 1 into station 3. This may be repeated to 40 minutes if necessary.

Caudal dose: With onset of need for block of lower sacral nerves (sometimes adequately blocked with time by the transition dose), 5 ml of ½ strength peridural solution are given from station 4 syringe into station 6. Four ml more of this caudal solution is next drawn up into station 4 syringe, and this dose may then be repeated in 40 minutes prn.

II. Full-Strength Solution for First and Second Stages (this is for instances where labor is hard and rapid delivery is expected)

Transition dose [skipped].

Caudal dose: station 1 syringe is used to give 5 ml solution quickly into station 3.

III. Full-Strength Solution for First Stage and ¾ Solution for Second (this is for instances of previous easy labor and delivery Transition dose [skipped]

Caudal dose: Five ml of the ½ strength peridural solution from station 4 syringe is injected into the station 6 caudal tubing containing 2½ ml peridural solution, thereby administering a peridural solution in dose of ¾ strength B. Modification of double-catheter method [per Bonica and McDonald, ref.-] for three solutions, using the drug bupivacaine. The above authors recommend the use of bupivacaine, a solution which, while not localizing quite as well, is readily available commercially—in three concentrations: 0.25 percent, 0.125 percent, and 0.5 percent. The equipment as described readily adapts to the three distinct solutions. There are two easily-applied options:

(1) Bupivacaine bottles mounted on the apparatus are 0.25 percent for station 1, and 0.5 percent for station 4. A separate syringe of 0.125 percent bupivacaine is preliminarily substituted for the station 4 syringe to fill the 4½ ml capacity caudal tubing of station 6 with that solution. The original station 4 syringe is reattached to station 4 and 4–5 ml 0.5 percent bupivacaine are drawn up. Four-five ml doses of 0.25 percent bupivacaine peridural are given (station 1 to station 2) from the beginning, and repeated as necessary. For transition pain, the syringe on station 4 injects injects 4½ cc 0.5 percent solution into the caudal tubing, expelling the contained 0.125 percent solution. The next caudal dose will be 0.5 percent solution.

(2) As above, the vials assembled to the apparatus are 0.25 percent bupivacaine for peridural, and 0.5 or 1 percent for caudal. Peridural and caudal tubings are filled with solutions from their respective vials (station 1 and station 4, respectively), and solution is drawn into the syringes. A separate syringe with 4–5 ml 0.125 percent bupivacaine is kept aside. As before, the main and follow up peridural doses are given as 0.25 percent solution. When the transition dose is needed, Luer-lok connector on the caudal tubing is loosed, and 4–5 ml 0.125 percent bupivacaine injected directly into the caudal catheter. This transition dose can be repeated in the same manner pm. When the caudal dose is required, it is given within the apparatus by using the syringe of station 4 to inject station 6 with 3–4 ml. This, again, can be repeated prn.

C. Use of the Peridural-Caudal Apparatus and Principle for Surgery

As aforementioned, localized segmental blocks are applicable for many operations below approximately the level of the nipples. It has been especially applicable to complex gynecological "above-and-below" procedures, such as abdominal hysterectomy and vaginal repairs, and radical hysterectomies. In these cases, lower thoracic and upper lumbar segments are blocked for the abdominal part of the procedure, and the sacral segments for vagina and related structures. While stronger and more penetrant solutions are required for surgery, localization was sufficiently good with Cleland solutions that many cases in the latter part of the series were able to lift themselves awake and without pain from the surgical table onto the gurney after several hours of surgery. Blood pressures showed unusual stability during the procedures.

Solutions were 1 percent lidocaine plain for test dose, 2 percent lidocaine for induction, containing 5 mcg per cc epinephrine and 2 mcg per cc norepinephrine, and, for maintenance, mepivacaine 1.5 percent, containing the same concentrations of E. and NE. After anesthetic test doses and checking of dermatomes, patient received a peridural induction dose of 5 to 6 ml lidocaine, followed by a reinforcing dose of the same quantity 4 to 5 minutes later. The first maintenance dose of mepivacaine was 4 ml 25 minutes later, followed by the same as a reinforcing dose in 3 to 5 minutes, with the same sequence repeated starting 25 minutes later, until the end of the surgery. For the caudal dose, the mepivacaine was used, reinforced once in 4–5 minutes. If this were strictly an abdominal case of usual length, it was found usually unnecessary to repeat the caudal dose. If a longer case, or where there is vaginal resection, a 3 cc dose of the mepivacaine would be repeated about every 30 minutes.

D. Use of Localizing Segmental Peridural and Caudal Blocks for Post-Operative Analgesia In almost 300 major surgical cases of the originators of this method, the technique was used for control of pain after surgery for 48 hours. In these cases, either tetracaine 0.19%, mepivacaine 1.5 percent or the standard OB solution was used,—always with the same concentrations of E. and NE. Patients were able to deep breathe and cough without pain, and be ambulated.

It should be noted that use of the double-catheter method for surgery and postoperative analgesia is not as useful for pelvic operations when solutions of lesser localization and penetrance are used. As manufacturers develop solutions of better localization, an advantage will be more evident, and desirable from the physiological point of view.

We claim:

1. A fluid delivery device comprising:
   an outer housing having a first input port, a first output port and a first fluid measuring device port;
   a cylindrical channeling member located substantially within the outer housing;

wherein the channeling member has internal conduit structure enabling the channeling member, when rotated relative to the outer housing, to be selectively positioned at first, second and third positions, such that the first fluid measuring device port communicates with the first input port when the channeling member is at the first position, the first fluid measuring device port communicates with the first output port when the channeling member is at the second position, and the first fluid measuring device port communicates with no port when the channeling member is at the third position;

wherein the outer housing has a second output port, the channeling member being rotatable to a fourth position, the conduit structure of the channeling member allowing communication between the first fluid measuring device port and the second output port when the channeling member is at the fourth position; and wherein the outer housing has a second input port a third output port and a second fluid measuring device port, the channeling member being rotatable to fifth, sixth and seventh positions relative to the housing, the conduit structure of the channeling member allowing communication between the second input port and the second fluid measuring device port when the channeling member is in the fifth position, communication between the second fluid measuring device port and the third output port when the channeling member is in the sixth position, and communication between the second fluid measuring device and the second output port when the channeling member is in the seventh position.

2. The device of claim 1 further comprising a fluid measuring device connected to the fluid measuring device port.

3. The device of claim 1 further comprising a dial connected to the cylindrical channeling member and manually manipulable to rotate the channeling member to different positions.

4. The device of claim 1 wherein the housing and the channeling member are made of injection molded polymer resin.

5. A fluid delivery device comprising:

an outer housing having a first input port, a first output port and a second output port;

a cylindrical channeling member located substantially within the outer housing;

wherein the channeling member can be selectively rotated relative to the outer housing to first, second and third positions, the channeling member having a conduit structure allowing communication between the first input port and the first output port when the channeling member is in the first position, communication between the first input port and the second output port when the channeling member is in the second position and no communication between any of the ports when the channeling member is in the third position;

wherein the first input port is connectable to a first fluid measuring device, the housing having a second input port and the channeling member being rotatable to a fourth position relative to the housing, the conduit structure of the channeling member allowing communication between the first and second input ports when the channeling member is at the fourth position so that fluid can be delivered from the second input port to any one of the output ports via a fluid measuring device connected to the first input port by selectively positioning the channeling member relative to the housing; and wherein the housing has a third input port, a fourth input port and a third output port, the channeling member being rotatable to fifth, sixth and seventh positions, the conduit structure of the channeling member allowing communication between the third and fourth input ports when the channeling member is at the fifth position, communication between the fourth input port and the third output port when the channeling is at the sixth position, and communication between the fourth input port and the second output port when the channeling member is in the seventh position.

6. The device of claim 5 further comprising first and second fluid measuring devices, the first fluid measuring device being connected to the first input port and the second fluid measuring device being connected to the fourth input port so that the first and fourth input ports function as fluid measuring device ports.

* * * * *